United States Patent [19]

Bianchi et al.

[11] Patent Number: 4,500,731
[45] Date of Patent: Feb. 19, 1985

[54] DERIVATIVES OF 4-PHENYL-4-OXOBUTEN-2-OIC ACID, PHARMACEUTICAL COMPOSITIONS CONTAINING THEM, AND THERAPEUTIC USES FOR THEM

[75] Inventors: Mario Bianchi; Fernando Barzaghi, both of Milan, Italy

[73] Assignee: Roussel Uclaf, Romainville, France

[21] Appl. No.: 435,464

[22] Filed: Oct. 20, 1982

[30] Foreign Application Priority Data

Oct. 22, 1981 [IT] Italy ............................. 49547 A/81

[51] Int. Cl.³ .............................................. C07C 59/90
[52] U.S. Cl. ...................... 514/452; 560/53; 549/362; 514/568; 514/545; 562/463
[58] Field of Search .................. 182/463; 560/57; 549/362; 424/308, 317, 244

[56] References Cited

U.S. PATENT DOCUMENTS 4,058,558 11/1977 Cousse et al. ...................... 562/463

OTHER PUBLICATIONS

Child, Ralph G., et al., "Fenbufen, a New Anti-Inflammatory Analgesic: Synthesis and Structure-Activity Relationships of Analogs", *Journal of Pharmaceutical Sciences,* vol. 66, No. 4, Apr. 1977, pp. 466-476.

Markovac, A., et al., "Antimalarials. 3. 2,6-Bix(aryl)-4-pyridinemethanols with Trifluoromethyl Substituents", *Journal of Medicinal Chemistry,* vol. 15, No. 9, Sep. 1972, pp. 918-922.

Pettit, George R., et al., "Bufadienolides. 1. Introduction and Base-Catalyzed Condensation of Methyl Ketones with Glyoxylic Acid", *Journal of Organic Chemistry,* vol. 235, No. 5, May 1970, pp. 1367-1376.

Rice, Grace Potter, "The Isomeric Esters of Para-Ethoxy-Benzoylacrylic Acid", J.A.C.S., vol. 46, No. 10, Oct. 1924, pp. 2319-2326.

Journal of the American Chemical Society, vol. 71, No. 4, Apr. 1949, F. K. Kirchner, et al., pp. 1210-1213.

Journal of the American Chemical Society, vol. 70, No. 10, Oct. 1948, D. Papa et al., pp. 3356-3360.

Journal of American Pharmaceutical Association, vol. 37, No. 11, Nov. 1948, pp. 439-449.

*Primary Examiner*—Paul J. Killos
*Attorney, Agent, or Firm*—Stevens, Davis, Miller & Mosher

[57] ABSTRACT

A compound of the formula I:

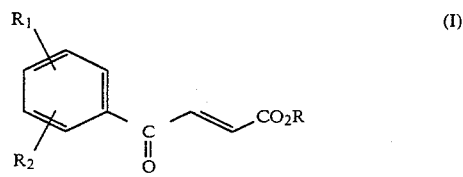

in which $R_1$ and $R_2$ in any position on the benzene ring are different from each other, and independently represent a hydroxy group or an alkoxy group containing from 1 to 8 carbon atoms, or else $R_1$ and $R_2$ together form an —$OCH_2CH_2O$—radical, and R represents a hydrogen atom or an alkyl group containing from 1 to 8 carbon atoms, as well as the alkali metal, alkaline earth metal, ammonium or amine salts of the said products of formula I in which R represents a hydrogen atom. These compounds have been found useful in the treatment of hyperchlorhydria, gastric and gastro-duodenal ulcers, gastritis, hiatal hernias, and gastric and gastroduodenal ailments accompanied by gastric hyperacidity. Pharmaceutical compositions including these compounds are disclosed along with methods for their production.

17 Claims, No Drawings

DERIVATIVES OF 4-PHENYL-4-OXOBUTEN-2-OIC ACID, PHARMACEUTICAL COMPOSITIONS CONTAINING THEM, AND THERAPEUTIC USES FOR THEM

The present invention concerns derivatives of 4-phenyl 4-oxo 2-butenoic acid, their salts, their method of preparation, their use as drugs and compositions containing them.

The object of the invention is a compound of formula I:

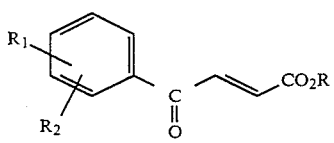
(I)

in which R represents a hydrogen atom or an alkyl group containing from 1 to 8 carbon atoms, and $R_1$ and $R_2$ in any position on the benzene ring, are different from each other, and independently represent a hydroxy group or an alkoxy group containing from 1 to 8 carbon atoms, or else $R_1$ and $R_2$ together form an $-OCH_2CH_2O-$ radical, as well as the alkali metal, alkaline earth metal, ammonium or amine salts of the compound of formula I when R represents a hydrogen atom.

When $R_1$ or $R_2$ represents an alkoxy radical it is preferably the methoxy, ethoxy or n-propoxy radical.

When R represents an alkyl radical, it is preferably the methyl, ethyl, n-propyl, isopropyl, n-butyl, isobutyl, terbutyl or n-pentyl radical.

The compounds of formula I, which have a double bond, may be in the form of a cis or trans geometric isomer and these different isomers fall, of course, within the scope of the invention.

The alkali metal or alkaline earth metal salts of the compounds of formula I in which R represents a hydrogen atom can be the sodium, potassium, lithium or calcium salts.

The amine salts of the products of formula I in which R represents a hydrogen atom are the usual amine salts. Among these are monoalkylamines such as methylamine, ethylamine and propylamine, dialkylamines such as dimethylamine, diethylamine and di-n-propylamine, and trialkylamines such as triethylamine. Other useful amines are piperidine, morpholine piperazine and pyrrolidine.

The invention is particularly directed to compounds of formula I as defined above in which R represents a hydrogen atom as well as their alkali metal, alkaline earth metal, ammonium or amine salts, as well as those in which one of $R_1$ and $R_2$ represents a hydroxy group and the other a methoxy group.

The preferred compounds of the invention are (E) 4-(3-methoxy-4-hydroxyphenyl)-4-oxobuten-2-oic acid and (E) 4-(2-hydroxy-4-methoxyphenyl)-4-oxobuten-2-oic acid.

Another object of the invention is a method of preparing the compounds of formula I which is characterized by reacting glyoxylic acid with a compound of formula II:

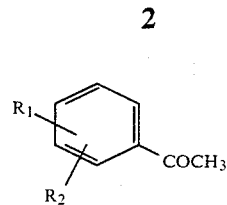
(II)

in which $R_1$ and $R_2$ have the same meaning as above, in the presence of a dehydrating agent in order to obtain the corresponding compound of formula I in which R represents a hydrogen atom. If desired, this is subjected to the action of an esterification agent in order to obtain a compound of formula I in which R represents an alkyl radical containing from 1 to 8 carbon atoms. Also, the alkali metal, alkaline earth metal, ammonium or amine salts may be formed instead of performing the esterification. The salts may be formed through reaction with a suitable base.

Still another object of the invention is a variation of the above process which is characterized by reacting a compound of formula III

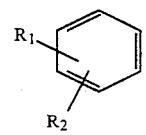
(III)

in which $R_1$ and $R_2$ retain the same meaning as above, with maleic anhydride in order to obtain the corresponding compound of formula I in which R represents a hydrogen atom.

In a preferred embodiment of the process of the invention:

the dehydration agent is an acid, such as acetic acid;

the base which, if desired, reacts withe the compound of formula I in which R represents a hydrogen atom is, for instance, sodium hydroxide, potassium hydroxide, lithium hydroxide, calcium hydroxide, sodium ethylate, potassium ethylate, ammonia or an amine such as, for instance methyl amine, ethyl amine, propyl amine, dimethylamine, diethylamine, di-n-propylamine, triethylamine, piperidine, morpholine, piperazine or pyrrolidine;

the reaction with the base is preferably carried out in a solvent or a mixture of solvents such as water, ethyl ether, ethanol, acetone or ethyl acetate;

the esterification reaction takes place, for instance, by reacting the acid of formula I with an alcohol of formula R-OH in an acid medium such as hydrochloric, phosphoric, or paratoluene sulfonic acid.

The esterification can of course be carried out by other known methods, such as reacting the acid chloride in an alcohol, reacting the acid anhydride in an alcohol, or else by reacting the acid and alcohol in the presence of dicyclohexylcarbodiimide.

In a variation of the process, the reaction between the compound of formula III and the maleic anhydride takes place in the presence of aluminum chloride.

The compounds of formula I as well as their salts show useful pharmacological properties. They exhibit substantial anti-ulcer activity for treating ailments of the digestive tract. Furthermore, when they are in contact with the gastric mucosa they exhibit an anti-secretion activity and a cyto-protective activity. These properties, which will be further illustrated in the examples, justify the use of the compounds of formula I, or their pharmaceutically acceptable salts, as drugs.

An object of the invention is, therefore, to produce the compounds of formula I as well as their pharmaceutically acceptable alkali metal, alkaline earth metal, ammonium and amine salts, which are useful in treating gastric and gastro-duodenal ailments and disorders.

In particular, the object of the invention is the compound (E) 4-(3-methoxy-4-hydroxyphenyl)-4-oxobuten-2-oic acid as well as its pharmaceutically acceptable alkali metal, alkaline earth metal, ammonium or amine salts.

The compounds of the invention are used in human or animal therapy, particularly in the treatment of hyperchlorhydria, gastric or gastro-duodenal ulcers, gastritis, hiatal hernias, and gastric or gastro-duodenal ailments accompanied by gastric hyperacidity. Of course, compositions containing these compounds are also useful in the treatments.

The dose, which varies in accordance with the product used and the ailment in question may range, for instance, between 0.05 and 2 g/day in adults per os.

Another object of the present application is a pharmaceutical composition which contains at least one of the compounds of formula I as an active principle. These compositions are prepared in such a manner that they can be administered by a digestive (oral or rectal) or parenteral route.

The compositions may be solid or liquid and can be present in the pharmaceutical forms currently used in human or animal medicine, such as simple or coated tablets, capsules, granules, suppositories and injectable preparations. These are prepared by the usual methods.

The active principle or principles may be incorporated in excipients generally employed in pharmaceutical compositions such as talc, gum arabic, lactose, starch, magnesium stearate, cocoa butter, aqueous or non-aqueous vehicles, animal or vegetable fats, paraffin derivatives, glycols, various wetting, dispersing or emulsifying agents and preservatives.

The following examples illustrate the invention without, however, limiting it.

EXAMPLE 1

(E) 4-(3-methoxy-4-hydroxyphenyl)-4-oxobuten-2-oic acid

A mixture containing 8.5 g of acetovanillone, 5.6 g of glyoxylic acid monohydrate and 100 cc of acetic acid was heated at the boiling point for 20 hours. The reaction mixture was allowed to cool, then evaporated to dryness under reduce pressure and the residue taken up in either. A product was obtained which was filtered and recrystallized from a mixture of ethyl acetate and petroleum ether (60:50). This yield 2.7 g of the desired product, melting at 164°–165° C.

EXAMPLE 2

(E) 4-(2,3-dihydrobenzodioxine-6-yl)-4-oxobuten-2-oic acid 10.2 g of 2,3-dihydrobenzodioxine were added to a suspension containing 37.5 g of aluminum chloride and 8 g or maleic anhydride in 100 cc of dichloroethane. Stirring was effected for 8 hours, whereupon it was set aside overnight. The reaction mixture was poured into normal hydrochloric acid and filtered. After recrystallization from ethanol, the desired product, melting at 186°–187° C., was obtained.

EXAMPLE 3

(E) 4-(2-hydroxy-4-methoxyphenyl)-4-oxobuten-2-oic acid

Proceeding in the same manner as in Example 1, starting with glyoxylic acid and 2-hydroxy 4-methoxy acetophenone, the desired product melting at 178°–181° C. was obtained.

EXAMPLE 4

(E) 4-(2-hydroxy-5-methoxyphenyl)-4-oxobuten-2-oic acid

Proceeding in the same manner as in Example 1, starting with glyoxylic acid and 2-hydroxy 5-methoxy acetophenone, the desired product was obtained.

EXAMPLE 5

4-(2-hydroxy-6-methoxyphenyl)-4-oxobuten-2-oic acid

Operating in the same manner as in Example 1, starting from glyoxylic acid and 2-hydroxy 6-methoxy acetophenone, the desired product was obtained.

Pharmaceutical Forms

EXAMPLE 6

TABLETS

Tablets were prepared having the following formula:
product of Example 1: 100 mg
excipient q.s. for a finished tablet of: 300 mg
(details of the excipient: lactose, wheat starch, processed starch, rice starch, magnesium stearate, talc).

EXAMPLE 7

CAPSULES

Capsules of the following formula were prepared:
product of Example 1: 100 mg
excipient q.s. for a finished capsule of: 300 mg
(details of the excipient: talc, magnesium stearate, aerosil).

Pharmacological Study (1) Determination of the anti-gastric secretion activity

The technique used is described by H. SHAY et al. in Gastroenterology, 5, 43, (1945).

Male rats were used weighing about 200 g (10 animals per lot) which had been without food for 48 hours but were allowed an 8% glucose solution ad libitum. After the rats were slightly anesthetized with ether, the pylorus of each was ligated. After the end of the operation, the compound to be tested was administered intraduodenally in different doses, or in the case of the control animals, a 0.5% solution of carboxymethylcellulose was administered intraduodenally, after which the abdominal incision was sutured.

Three hours later, the animals were sacrificed and their stomachs removed, after ligating the esophagus. The gastric juice was removed and centrifuged. The volume of gastric juice was then determined and the total acidity was established by titrating a 100 $\mu$l sample of gastric juice to a pH of 7 by means of 1/10 N aqueous sodium hydroxide solution.

The percentages of variation in total acidity between gastric secretions of the test and control animals were calculated, with the results appearing below.

(2) Determination of anti-ulcer activity

Stress Ulcer

The technique consists in inducing ulcers in the stomachs of rats by stress (stress and cold). The technique used is described by E. C. SENAY and R. J. LEVINE, Proc. Soc. Exp. Biol., 124, 1221 (1967).

Female rats of 150 g were used (5 animals per lot) which have fasted for 48 hours with water ad libitum and glucose solution for 8 hours. The animals were given the compound being tested, or 0.5% solution of carboxymethylcellulose for the control animals, by esophageal tube. Two hours later the animals were bundled in a jacket of netting. Their paws were tied and the entire unit was placed in a refrigerator at 8° C. for two hours. The rats were released and killed with ether.

Their stomachs were opened along the greater curvature and examined with a binocular magnifier. The seriousness of the lesions was rated from 0 to 3 for each stomach.

For each lot of the rats, the average intensity of the ulcerations was determined. The degree of ulceration for the test animals was determined and compared with the control animals for each lot.

The results were expressed in percentage and are set forth in the table appearing below.

(3) Determination of acute toxicity

The $LD_{50}$ was evaluated after administration of the products orally in mice.

The results are set forth in the table appearing below.

| | | RESULTS Anti-secretion and anti-ulcer activity (% variation as compared with the controls) | |
|---|---|---|---|
| Product of Example | $LD_{50}$ mg/kg | Doses mg/kg  Acid conc. | Ulceration |
| 1 | 1000 | 10    −90 | −89 |
| 2 | 750 | 10    −41 | −33 |

What is claimed is:

1. A compound of formula I:

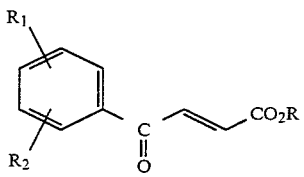

(I)

in which R represents a hydrogen atom or an alkyl group containing from 1 to 8 carbon atoms, and $R_1$ and $R_2$ in any position on the benzene ring are different from each other and independently represent a hydroxy group or an alkoxy group containing from 1 to 8 carbon atoms, or else $R_1$ and $R_2$ together form an —OCH$_2$CH$_2$O— radical, as well as the alkali metal, alkaline earth metal, ammonium or amine salts of the said product of formula I when R represents a hydrogen atom.

2. A compound of formula I as defined in claim 1 wherein R represents a hydrogen atom, or alkali metal, alkaline earth metal, ammonium or amine salts thereof.

3. A compound of the formula I as defined in claim 1 in which one of $R_1$ and $R_2$ represents a hydroxy group and the other a methoxy group.

4. A compound of the formula I as defined in claim 2 in which one of $R_1$ and $R_2$ represents a hydroxy group and the other a methoxy group.

5. A compound of formula I as defined in claim 3, which is: (E) 4-(3-methoxy-4-hydroxyphenyl)-4-oxobuten-2-oic acid.

6. A pharmaceutical composition for treatment of hyperchlorhyria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 1; and
a pharmaceutically acceptable excipient.

7. A pharmaceutical composition for treatment of hyperchlorhyria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 2; and
a pharmaceutically acceptable excipient.

8. A pharmaceutical composition for treatment of hyperchlorhyria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 3; and
a pharmaceutically acceptable excipient.

9. A pharmaceutical composition for treatment of hyperchlorhyria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 4; and
a pharmaceutically acceptable excipient.

10. A pharmaceutical composition for treatment of hyperchlorhyria, gastric or gastro-duodenal ulcers, gastritis, hiatal hernias, or gastric or gastro-duodenal ailments accompanied by gastric hyperacidity, comprising:
a therapeutically effective amount of a compound of formula (I) as claimed in claim 5; and
a pharmaceutically acceptable excipient.

11. A method of treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a thereapeutically effective amount of a compound as defined in claim 1.

12. A method of treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 2.

13. A method of treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 3.

14. A method of treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 4.

15. A method of treating a patient suffering from hyperchlorhydria, gastric or gastro-duodenal ulcers, gastritis, hiatal hernias, or gastric or gastro-duodenal ailments accompanied by gastric hyperacidity, comprising administering to said patient a therapeutically effective amount of a compound as defined in claim 5.

16. A method as claimed in claim 11, herein said compound is administered by digestive route.

17. A method as claimed in claim 11, wherein said compound is administered parenterally.

* * * * *